US009914953B2

(12) United States Patent
Gupta et al.

(10) Patent No.: US 9,914,953 B2
(45) Date of Patent: *Mar. 13, 2018

(54) METHOD AND APPARATUS FOR INOCULATING AND STREAKING A MEDIUM IN A PLATE

(71) Applicant: LBT INNOVATIONS LIMITED, Adelaide (AU)

(72) Inventors: Rajiv Gupta, Cupertino, CA (US); Stephen Lewis Leckenby, Victoria (CA); Phillip James Duncan, Mount Waverley (AU); Ryan Andrew Annear, South Carlton (AU); Daniel Patrick Torpy, Surrey Hills (AU); Chong Kean Ooi, Glen Waverley (AU); Michael John Tomlinson, Ringwood East (AU); Leon Raj, Ferntree Gully (AU); Graeme John Cross, North Fitzroy (AU); Kenneth Andrew Nicoll, Doncaster (AU); Wayne Richard Cheetham, Blackburn (AU); Michael Craig Lovett, Blackburn South (AU); Colin William Potter, Nunawading (AU)

(73) Assignee: LABTECH SYSTEMS LTD, Adelaide SA (AU)

( * ) Notice: Subject to any disclaimer, the term of this patent is extended or adjusted under 35 U.S.C. 154(b) by 101 days.

This patent is subject to a terminal disclaimer.

(21) Appl. No.: 14/203,136

(22) Filed: Mar. 10, 2014

(65) Prior Publication Data

US 2014/0186932 A1    Jul. 3, 2014

Related U.S. Application Data

(63) Continuation of application No. 12/520,970, filed as application No. PCT/AU2008/000016 on Jan. 11, 2008, now Pat. No. 8,691,558.

(30) Foreign Application Priority Data

Jan. 12, 2007   (AU) ................................ 2007900146

(51) Int. Cl.
*C12M 1/26*   (2006.01)
*C12Q 1/24*   (2006.01)
(Continued)

(52) U.S. Cl.
CPC .............. *C12Q 1/24* (2013.01); *C12M 33/02* (2013.01); *C12M 33/06* (2013.01); *C12M 41/48* (2013.01)

(58) Field of Classification Search
CPC ...... C12M 23/10; C12M 23/50; C12M 33/02; C12M 33/06; C12M 41/48; C12C 1/24
See application file for complete search history.

(56) References Cited

U.S. PATENT DOCUMENTS

| 3,455,788 A | 7/1969 | Curry et al. |
| 3,623,958 A | 11/1971 | Fitzgerald |

(Continued)

FOREIGN PATENT DOCUMENTS

| CA | 1286621 C | 7/1991 |
| DE | 19520420 A1 | 12/1996 |

(Continued)

Primary Examiner — William H Beisner
(74) Attorney, Agent, or Firm — Seager, Tufte & Wickhem LLP

(57) ABSTRACT

An apparatus for inoculating and streaking a solid growth culture medium in a plate, the streaking using a streaking applicator having a line of resiliently and flexibly supported spaced apart contact surfaces, the apparatus including:
(a) an inoculating and streaking station including:
  a plate work position having a notional action line fixed in two dimensions (x,y) in a predetermined position; and (Continued)

a plate rotation device for rotating a positioned plate to cause streaking;

(b) a sensor capable of locating the surface of the medium in a positioned plate to thereby determine for that plate, prior to inoculation and streaking of that plate, the third dimension (z) of the action line;

(c) an inoculating device capable of dispensing inoculum, along the action line, on the surface of the medium in the positioned plate; and (d) a streaking device capable of moving the streaking applicator such that its line of spaced apart contact surfaces contacts, along the action line, the surface of the medium in the positioned plate, prior to rotation of the positioned plate for streaking.

16 Claims, 7 Drawing Sheets

(51) Int. Cl.
*C12M 1/30* (2006.01)
*C12M 1/32* (2006.01)
*C12M 1/36* (2006.01)

(56) References Cited

U.S. PATENT DOCUMENTS

| | | |
|---|---|---|
| 3,632,478 A | 1/1972 | Fink |
| 3,660,243 A | 5/1972 | Young |
| 3,778,351 A | 12/1973 | Rosov |
| 3,788,951 A | 1/1974 | von der Pfordten |
| 3,799,844 A | 3/1974 | Campbell et al. |
| 3,830,701 A | 8/1974 | Stussman et al. |
| 3,844,896 A | 10/1974 | Sharpe |
| 3,850,754 A | 11/1974 | Wilkins et al. |
| 3,902,972 A | 9/1975 | Beckford |
| 3,935,075 A | 1/1976 | Perry et al. |
| 3,962,040 A | 6/1976 | Campbell et al. |
| 4,010,077 A | 3/1977 | Pardos |
| 4,102,748 A | 7/1978 | Vacanti |
| 4,144,135 A | 3/1979 | Sequeira |
| 4,170,861 A | 10/1979 | Snyder et al. |
| 4,273,877 A * | 6/1981 | Anagnostopoulos .. C12M 33/04 435/286.3 |
| 4,287,301 A | 9/1981 | Castle |
| 4,613,573 A | 9/1986 | Shibayama et al. |
| 4,687,746 A | 8/1987 | Rosenberg et al. |
| 4,892,831 A | 1/1990 | Wong |
| 4,981,802 A | 1/1991 | Wylie et al. |
| 5,036,001 A | 7/1991 | Gork et al. |
| 5,106,584 A | 4/1992 | Funakubo et al. |
| 5,206,171 A | 4/1993 | Dillon et al. |
| 5,629,201 A | 5/1997 | Nugteren et al. |
| 5,691,195 A | 11/1997 | Doleans et al. |
| 5,695,988 A | 12/1997 | Chong |
| 5,756,304 A | 5/1998 | Jovanovich |
| 6,291,234 B1 | 9/2001 | Raz et al. |
| 6,521,190 B1 | 2/2003 | Edens et al. |
| 6,617,146 B1 | 9/2003 | Naccarato et al. |
| 6,843,962 B2 | 1/2005 | Haslam |
| 7,115,384 B2 | 10/2006 | Clark et al. |
| 7,205,158 B2 | 4/2007 | Pankratz et al. |
| 7,709,268 B1 | 5/2010 | Edwards et al. |
| 7,829,021 B2 | 11/2010 | Hutchins et al. |
| 7,863,034 B2 | 1/2011 | Glasson et al. |
| 8,691,558 B2 | 4/2014 | Gupta et al. |
| 2002/0064867 A1 | 5/2002 | Clark et al. |
| 2002/0120214 A1 | 8/2002 | Cole |
| 2007/0202564 A1 | 8/2007 | Glasson et al. |
| 2008/0318310 A1 | 12/2008 | Dufresne et al. |

FOREIGN PATENT DOCUMENTS

| | | |
|---|---|---|
| EP | 0242114 A2 | 10/1987 |
| FR | 2668495 A1 | 4/1992 |
| GB | 2025457 A | 1/1980 |
| GB | 2255407 A | 11/1992 |
| GB | 2247076 A | 2/1999 |
| JP | 01191678 A | 8/1989 |
| JP | 02072898 A | 3/1990 |
| JP | 0361476 A | 3/1991 |
| JP | 03049676 A | 3/1991 |
| JP | 03133375 A | 6/1991 |
| JP | 03175996 A | 7/1991 |
| JP | 04234973 A | 8/1992 |
| JP | 04248980 A | 9/1992 |
| JP | 05225995 A | 9/1993 |
| JP | 05344535 A | 12/1993 |
| JP | 06225753 A | 8/1994 |
| JP | 06296481 A | 10/1994 |
| JP | 0767695 A | 3/1995 |
| JP | 07170970 A | 7/1995 |
| JP | 10004952 A | 1/1998 |
| JP | 10309199 A | 11/1998 |
| JP | 11346796 A | 12/1999 |
| JP | 2001149062 A | 6/2001 |
| JP | 2001149063 A | 6/2001 |
| JP | 2001153761 A | 6/2001 |
| JP | 2002098704 A | 4/2002 |
| JP | 3414431 B2 | 6/2003 |
| JP | 2005052069 A | 3/2005 |
| JP | 2008166201 A | 7/2008 |
| WO | 8808024 A1 | 10/1988 |
| WO | 0018879 A1 | 4/2000 |
| WO | 0166686 A1 | 9/2001 |
| WO | 2004022245 A1 | 3/2004 |
| WO | 2005071055 A1 | 8/2005 |
| WO | 2008083439 A1 | 7/2008 |

* cited by examiner

METHOD AND APPARATUS FOR INOCULATING AND STREAKING A MEDIUM IN A PLATE

FIELD OF THE INVENTION

The present invention relates to the inoculation of solid growth culture media with a microbiological sample, and the subsequent streaking of the inoculum to produce isolated bacterial colonies, principally for diagnostic purposes such as medical diagnostic purposes. The present invention particularly relates to both a method and an apparatus for use in a microbiological laboratory.

BACKGROUND OF THE INVENTION

The isolation of individual colonies of micro-organisms (and in particular bacteria) is an important procedure in many microbiological laboratories. Traditionally, this isolation of bacteria has been performed manually by skilled laboratory technicians who first dispense a microbiological sample onto the surface of a solid growth culture medium, such as agar in a Petri dish (which will hereafter simply be referred to as a "medium" in an "agar plate" or simply in a "plate"), followed by the use of a hand-tool to spread the sample across the surface of the medium (called "streaking").

The hand-tool typically includes a terminal loop to make multiple streaks of increasing dilution of the inoculum across the medium. The streaks of increasing dilution tend to provide, generally towards the tail of the streaks, a number of single cells that allow for the growth of isolated microbiological colonies after incubation. These isolated colonies may then be analysed for colony morphology, and may undergo staining and other procedures which are necessary for determining, for example, the genus, the species and the strain of the previously unidentified organism.

Such inoculation and streaking is highly repetitious and in many pathology diagnostic microbiology laboratories is usually conducted in very high volumes, such as in volumes as high as 1,000 to 15,000 plates per day. It is tedious and laborious work that therefore is prone to error and inaccuracies. It is quite obviously work that would lend itself to either partial or full automation.

The literature is replete with suggestions for how best to automate these laboratory functions, yet very few of these suggestions have ever actually found success in a commercial laboratory environment. It therefore appears that the successful enablement of suitable laboratory apparatus has to date, for most, proved elusive.

A sample of patent documents that, since the early 1970's, have suggested different apparatus for automating the inoculation and streaking of solid growth media are U.S. Pat. No. 3,778,351 (R. J. Rosov) titled "Automatic Bacterial Specimen Streaker", U.S. Pat. No. 3,844,896 (A. N. Sharpe) titled "Apparatus for Performing Bacteriological Tests Automatically", U.S. Pat. No. 3,850,754 (J. R. Wilkins et al) titled "Automatic Inoculation Device", U.S. Pat. No. 3,935,075 (R. C. Perry et al) titled "Automatic Bacterial Specimen Streaker and Method for Using Same", U.S. Pat. No. 4,144,135 (P. J. L. Sequeira) titled "Spreader Device and Method of Spreading Inoculant", U.S. Pat. No. 4,287,301 (T. W. Astle) titled "Method and Apparatus for Streaking Agar", and U.S. Pat. No. 4,613,573 (K. Shibayama et al) titled "Automatic Bacterial Colony Transfer Apparatus". To the best of the applicant's knowledge, none of these suggestions have been successfully enabled, and thus suitable automation is still not available for such inoculating and streaking.

Three further, more recent, suggestions from the prior art require some discussion. They are the suggestions made by Vista Laboratories Ltd in U.S. Pat. No. 4,981,802 (C. Wylie et al) titled "Method and Apparatus for Streaking a Culture Medium", the Canadian Space Agency in U.S. Pat. No. 6,617,146 (F. Naccarato et al) titled "Method and Apparatus for Automatically Inoculating Culture Media With Bacterial Specimens From Specimen Containers", and Medvet Science Pty Ltd in international patent publication WO2005/071055 titled "Microbial Streaking Device" (licensed to the present applicant).

The Wylie patent describes an apparatus that only partially automates the inoculation and streaking process, in that it provides an apparatus for streaking a solid growth culture medium that has been manually inoculated by a laboratory technician, with the laboratory technician manually identifying upon the side of a plate the physical location of the inoculum (which identifying mark is later sensed by the streaking mechanism to determine where to commence streaking from). Furthermore, the streaking mechanism suggested for use by Wylie is a complex multiple head mechanism that relies on multiple passes across the medium by a single-point tool so as to provide a sinuous streaking path. The Wylie apparatus is thus reasonably slow and provides only a partial response to the automation challenge.

The Naccarato patent describes an automated process for single-point inoculation of a solid growth culture medium (at any location on the surface) from one of a possible variety of different forms of specimen container, followed by the subsequent use of a traditional, single-point streaking tool again following a convoluted path across the surface of the medium to thereby spread the inoculum. So that the streaking tool knows where the inoculum will be on the surface, the Naccarato apparatus describes the use of a reasonably complex device for recording the precise location of the inoculum, once the inoculum is placed on the surface, for use in subsequently guiding the streaking tool to that recorded location. These intermediate recordal and guiding steps, intermediate in the sense that they occur between inoculation and streaking, appear to introduce an undue risk of error and also unnecessary delays in the overall process.

The Medvet Science publication seeks to improve the automation process by the use of a new form of streaking tool, which tool includes a line of spaced apart contact surfaces (for contact with the surface of solid growth culture media), the contact surfaces being resiliently flexibly supported by a common support member. This streaking tool permits greater spread of a larger volume of the inoculum across the surface of the medium with a single streaking pass, as well as larger areas of more gradually increasing dilution of the sample. The inoculating and streaking apparatus described in the Medvet Science publication suggests the use of a pressure sensor to determine when the contact surfaces of the streaking tool have contacted the surface of the medium, without describing how the streaking tool knows the location of the inoculum on the surface (in terms of both two dimensional and three dimensional space).

It is an aim of the present invention to provide an automated apparatus for the inoculation and streaking of a microbiological sample on the surface of a solid growth culture medium, together with a method for the inoculation and streaking of a microbiological sample on the surface of a solid growth culture medium.

Before turning to a summary of the present invention, it must be appreciated that the above description of the prior art has been provided merely as background to explain the context of the invention. It is not to be taken as an admission that any of the material referred to was published or known, or was a part of the common general knowledge in Australia or elsewhere.

It is also useful to provide an explanation of some of the terms that will be used to define the spatial relationship of the apparatus and various parts thereof. In this respect, spatial references throughout this specification will generally be based upon a plate ultimately being inoculated and streaked in an upright orientation, with the surface of the medium in the plate being generally flat and horizontal. With this environment as the basis, the apparatus and some parts thereof may then be defined with reference to the "horizontal", allowing further references to "upper" or "upwardly" and "lower" or "downwardly", and also to the "vertical". In this respect, the traditional geometric spatial reference to x,y and z dimensions, and then to the x direction (or axis), the y direction (or axis) and the z direction (or axis), will also be adopted, with the x and y directions lying generally horizontally and the z direction lying generally vertically.

Finally, some aspects of the present invention that may ultimately be claimed in isolation (and not in an in-use environment), may nonetheless be difficult to describe and understand in isolation. Thus, some of the following description does describe the invention and its embodiments in such an in-use environment (for example, with a plate carrying medium within the apparatus for the purposes of inoculation and streaking). Of course, it must be appreciated that the use of such description, and the use of the abovementioned spatial relationships, to define the present invention, is not to be seen as a limitation and certainly is not to be seen as a limitation only to the in-use environment, unless that is clearly stated to be the intention.

SUMMARY OF THE INVENTION

The present invention provides an apparatus for inoculating and streaking a solid growth culture medium in a plate, the streaking using a streaking applicator having a line of resiliently and flexibly supported spaced apart contact surfaces, the apparatus including:
(a) an inoculating and streaking station including:
   a plate work position having a notional action line fixed in two dimensions (x,y) in a predetermined position; and
   a plate rotation device for rotating a positioned plate to cause streaking;
(b) a sensor capable of locating the surface of the medium in a positioned plate to thereby determine for that plate, prior to inoculation and streaking of that plate, the third dimension (z) of the action line;
(c) an inoculating device capable of dispensing inoculum, along the action line, on the surface of the medium in the positioned plate; and
(d) a streaking device capable of moving the streaking applicator such that its line of spaced apart contact surfaces contacts, along the action line, the surface of the medium in the positioned plate, prior to rotation of the positioned plate for streaking.

The inoculating and streaking station (often hereafter simply referred to as the "station") is the location, defined by a structure, within the apparatus where the main functions of the apparatus occur, that structure being generally centered around the plate work position. In one form, the plate work position is provided by the physical location in the apparatus of the sensor, the sensor ideally being rigidly mounted to a main frame. In this form, a platform for supporting a plate is preferably able to be moved into and out of the plate work position (translated along, for example, the y axis) from a plate loading position, such that the plate supported in the platform becomes positioned in the plate work position operatively adjacent (which ideally is underneath) the sensor with its medium surface open upwardly.

The platform preferably includes a plate centering mechanism for ensuring the proper (and consistent) central positioning of a plate upon the platform, the plate centering mechanism preferably being driven by a suitably arranged cam device and including a plate clamping function. The platform also preferably provides at least one locating datum point or surface, the use for which will become evident below when describing the functioning of the sensor.

In this form, the plate rotation device is preferably also provided in association with the platform, the rotation device including a home flag which allows for the return of a rotated plate to a starting position. The provision of such a home flag is useful for operation of the method and apparatus of the present invention with "half" plates as opposed to "full" plates, a description of which will be provided below.

The inoculating and streaking station is of course also able to be accessed by both the inoculating device and the streaking device (in addition to the sensor, as described above) such that a plate positioned in the plate work position (throughout this specification referred to as a "positioned plate" and typically being a de-lidded plate or, in other words, a plate bottom) can be operatively accessed by each of the sensor, the inoculating device and the streaking device. With regard to the reference to "operative" access, it will be appreciated that the use of this word merely indicates that access by an element is to be such that that element is then able to perform its required function.

As mentioned above, the plate work position includes a notional action line fixed in two dimensions (x,y) in a predetermined position. This action line is herein referred to as being a "notional" action line given that it will not be a visible action line and also will not have a determined position in three dimensional space until the height of the surface of medium in a positioned plate is determined. Nonetheless, it is this action line that is operatively accessed by both the inoculating device, for dispensing of the inoculum, and the streaking device, for streaking of the inoculum, during operation of the apparatus.

In a preferred form, the predetermined (x,y) position of the action line will, with reference to a positioned plate, be located such that the action line will be a radial line for a circular plate. In this form, during streaking, the positioned plate can be rotated about its centre by the plate rotation device of the station such that the line of contact surfaces of the streaking applicator moves about the centre of the positioned plate across the surface of the medium. For a half-plate, two such radial lines would normally be determined, one for each half of the plate, such that two inoculum deposits can be made and two streaking operations conducted.

It will be appreciated that the height of medium, such as agar, within a plate will fluctuate depending upon many factors. For example, not only do different plate and solid growth culture medium suppliers invariably produce agar plates, for example, with a wide variety of surface heights from one supplier to the next, but even the same suppliers tend to supply their own plates with varying heights of media. Also, different compositions and ages of media used for this purpose tend also to produce plates with different media surface heights.

Therefore, and due to such fluctuations in height, it is generally not possible for an apparatus such as that of the present invention to rely upon the height of the surface of media in all plates to be the same (and thus be the same distance above, in one form of the invention, the locating datum surface of the platform mentioned above).

It is therefore not feasible for an inoculating device of such an automated apparatus to rely on being able to place inoculum upon the surface of media at the same location in three dimensional space for every plate to be processed thereby, and significant difficulties and complexities are introduced in an apparatus that does. Of course, there are also potential difficulties and complexities for the streaking device of such an automated apparatus in trying to place the contact surfaces of a streaking tool upon the surface (so as to spread the inoculum rather than to gouge the surface) of media at the same location for every plate in three dimensional space.

In relation to the inoculating device, it will be appreciated that the incorrect location of a dispensing tip on the inoculation device in the z dimension (height) will give rise to the inoculum being dispensed from too high (and thus not dispensing as required), or there being contact with the surface such that the tip gouges the surface of the medium. In relation to the streaking device, incorrect location of the contact surfaces in the z dimension (height) will give rise to there either being no contact with the inoculum whatsoever, or there being too much contact such that the streaking tool gouges tracks in the surface of the medium.

Accordingly, and as mentioned above, the apparatus of the present invention includes a sensor capable of locating the surface of the medium in a positioned plate to thereby determine for that plate, prior to inoculation and streaking of that plate, the third dimension (z) of the action line. The sensor is then able to determine the location of the surface of the medium in each positioned plate separately, after the plate is positioned but before inoculation, in order to cope with the possibility of surface height fluctuations and avoid the difficulties mentioned above.

In a preferred form, the sensor is able to sense the medium surface for a positioned plate and measure the distance to the medium surface. Then, the measured distance is referenced to a fixed datum level to determine a surface positional reference relative to that datum level in one dimension (z) for the surface in the positioned plate. In this manner, it will be appreciated that the surface can thus be located in at least the z dimension by virtue of the determination of this surface positional reference. This effectively determines the height of the medium in the plate, at least with reference to that datum level.

In this respect, the datum level is preferably a surface that forms a part of the plate platform upon which the plate is clamped and supported. Therefore, in this form, the determination of the surface positional reference effectively determines the surface height of the medium with reference to the plate platform upon which it rests.

This surface positional reference can then be used, together with the notional action line to determine a line in three dimensions (x,y,z) that is representative of a line across the surface in the positioned plate.

In a preferred form, the sensor and its mode of operation may include the additional step of setting an upper detection limit and a lower detection limit, in some forms with the upper detection limit above the datum level and the lower detection limit below the datum level, to define a detection range between the upper and lower limits. A detection range can provide a calibration opportunity and allows the identification of, for example, multiple calibration sub-ranges to be applied within the detection range.

For example, in some forms, it may not be necessary or desirable for the method to be able to determine if a plate positioned in the plate work position still includes its lid thereon, or perhaps has been placed in the plate work position upside down. Thus, by adopting a narrow detection range, where the upper limit is only just above where the surface of the medium is expected to be, and the lower limit is only just below where the surface of the medium is expected to be, the sensor will not function if the detectable height of the plate in the plate work position is outside this narrow range, due to the sensor detecting either the surface of the plate lid or the surface of the plate bottom.

Conversely, there may be situations where it is desirable to provide an alarm, for example, if a lidded or inverted plate is placed in the plate work position. If a suitably broad enough detection range has been set, the sensor will thus sense the presence of the lid wall or the bottom wall, and will measure the distance to that surface rather than to the surface of the medium in the plate. Thus, by the provision of a suitably broad detection range with calibration sub-ranges for alarm conditions (lidded plate or inverted plate, for example) and for non-alarm conditions (de-lidded upright plate), the calibration sub-ranges can cause the identification (by virtue of the determination of the surface positional reference and its presence in one of the alarm calibration sub-ranges) of an alarm condition as well as allow for the proper functioning of the method.

The notional three dimensional action line that is represented by a line across the surface of the medium in the positioned plate (located by the sensor in the manner just described), will be specific to the medium in that positioned plate only, and may be (and is actually likely to be) a different three dimensional action line compared to the surface of the next plate processed in the plate work position.

Finally with reference to the sensor, reference is made to the present applicant's international patent application filed on 11 Jan. 2008 titled "Method and Apparatus for Locating the Surface of Solid Growth Culture Media in a Plate", claiming priority from Australian provisional patent application 2007900147, the full content of which is hereby incorporated by reference, where the sensor in various forms is more fully described. From this co-pending application, it will also be appreciated that the sensor of the apparatus of the present invention may play additional roles in the operation of the apparatus, such as being able to identify an incorrectly orientated plate in the plate work position, or an empty plate work position (at a time in the operation when there should be a positioned plate), or a plate that has not yet been de-lidded (when de-lidding should already have occurred)

Having then utilized the sensor to determine the proper position of the action line for media in a given positioned plate in three dimensional space, the apparatus of the present invention is then able to inoculate along (either partly or completely along) that action line, on the surface of the medium in the positioned plate, and then move the streaking applicator such that its line of spaced apart contact surfaces contacts, again along that action line, at least the inoculum (and preferably also the surface of the medium itself) on the surface of the medium in the positioned plate, with a predetermined contact pressure that is suitable for the particular streaking tool being used and also for the composition of the inoculum and of the particular solid growth medium being used, such that the inoculum is spread as required and such that the streaking tool does not undesirably gouge the surface of the medium.

In this respect, and having stated that the line of contact surfaces of the streaking applicator is to be located "along the action line", it must be appreciated that strict geometric compliance with this language is not necessary. In particular, it will be appreciated that the line of contact surfaces of the streaking applicator may be positioned so that they contact the inoculum (and/or the surface) closely adjacent the action line, such that the subsequent rotation of the plate causes the streaking applicator to move through, and thereby spread, the inoculum. It is thus envisaged that the line of spaced apart contact surfaces will contact the surface either along the action line or closely behind the action line. The reference to "along the action line" throughout this specification, with respect to the streaking applicator, is thus to be understood to include this scenario.

The inoculating device of the apparatus of the present invention may thus be any device that is able to obtain and hold a biological sample, generally in a liquid form, and transfer that sample to the surface of a medium in a positioned plate. In one form, the inoculating device will include a reasonably typical pipette device mounted to a robot system so as to be movable in the z direction and at least one of the x,y directions (using the directional terminology adopted above). The pipette device preferably includes a disposable dispensing tip releasably secured to a pipette body, secured in a manner that permits easy disposal of the tip once inoculation has been affected.

The inoculating device is preferably programmable for various inoculum volumes, and includes a positional height (z direction) referencing system capable of determining in three dimensional space the height of the location of the dispensing tip relative to the locating datum surface of the platform mentioned above, and of course relative to the notional action line mentioned above.

The inoculating device may additionally include means for separately imaging the dispensing tip during various of the abovementioned range of actions, so as to be able to (for example) visually or electronically monitor for the presence of a tip prior to sampling. In this respect, in one form of the present invention, this imaging means may additionally provide the positional height (z direction) referencing system mentioned above.

The pipette robot system of the inoculating device is preferably able to move the pipette device to access the dispensing tip supply, a biological sample station, the plate work position in the inoculating and streaking station, and also a tip waste disposal chute, whilst also including suitable tip securing means that allows for a dispensing tip to be secured, used to obtain and hold sample, dispense sample, and then dispose of the used tip. It will thus be appreciated that the pipette robot system of the inoculating device will move the pipette through this entire range of actions for each of the plates being processed by the apparatus of the present invention.

Further, the streaking device mentioned above is preferably a separate device to the inoculating device, and is thus preferably provided by its own robot system that includes an applicator handling head suitable to obtain (from a supply cartridge) and hold a streaking applicator, and then transfer that applicator to the plate work position and adjacent a positioned plate (generally all in the x,y plane). The applicator handling head then must be able to move the applicator in the z direction to locate the line of contact surfaces of the applicator along the notional action line (and thus upon/within the inoculum on the surface of the medium in the position plate) as mentioned above.

Streaking applicators preferred for use with the above described automated streaking apparatus are the streaking applicators generally described in the abovementioned international patent publication WO2005/071055 (Medvet Science Pty Ltd) titled "Microbial Streaking Device" (licensed to the present applicant), the full content of which is herein incorporated by reference. These streaking applicators can be said to have a generally flat rectangular form, albeit with two major inclined portions that together form a very shallow inverted v-shaped body. An upper portion of the body provides a mounting portion and a lower portion of the body provides the line of spaced apart contact surfaces and a resilient and flexible support member.

With this in mind, the applicator handling head of the streaking robot system preferably includes an openable clamping member that is able to grasp and clamp the mounting portion of the applicators mentioned above, the applicators being provided in a supply cartridge of the type generally described in the present applicant's international patent application filed on 11 Jan. 2008 titled "A Streaking Applicator Cartridge and a System for Connecting Same to a Streaking Apparatus", claiming priority from Australian provisional patent application 2007900144, the full content of which is hereby incorporated by reference.

The openable clamping member of the streaking robot system preferably includes a release catch which is able to interact with a fixed eject pin located near an applicator disposal chute, such that engagement of the pin with the latch causes the clamping member to release the applicator and allow it to fall into the applicator disposal chute.

The present invention thus additionally provides a method for inoculating and streaking a solid growth culture medium in a plate, the streaking using a streaking applicator having a line of resiliently and flexibly supported spaced apart contact surfaces, the method including the steps of:
(a) placing a plate in a plate work position in an inoculating and streaking station, the plate work position having a notional action line fixed in two dimensions (x,y) in a predetermined position;
(b) locating the surface of the medium in the positioned plate to thereby determine for that plate, prior to inoculation and streaking of that plate, the third dimension (z) of the action line;
(c) dispensing inoculum along the action line on the surface of the medium in the positioned plate;
(d) moving the streaking applicator such that its line of spaced apart contact surfaces contacts, along the action line, the surface of the medium in the positioned plate; and
(e) rotating the positioned plate in the plate work position for streaking.

In a preferred form of the present invention, the apparatus and method includes an ability to handle plates in their normal laboratory configuration, which traditionally sees the plates stored before inoculation and streaking (hereafter referred to as "processing"), and also after processing, in an inverted orientation. By way of explanation, it is usual for solid growth culture medium plates to have a lid and a bottom and be stored upside-down such that their lids are facing downwardly and their bottoms (containing the agar) are stored uppermost. This is done to prevent any condensation that may form inside the lid from falling onto the medium surface, which would occur if the plates were not stored in an inverted orientation, thereby damaging the integrity of the medium and (after treatment) the microbiological inoculum.

Therefore, the apparatus of the present invention preferably additionally includes a plate supply capable of storing unprocessed plates (hereafter referred to as a "raw plate") in an inverted orientation, together with a plate transfer feed mechanism that is able to obtain an inverted raw plate from the plate supply, orientate the raw plate such that its bottom is lowermost and its lid is removed, and transfer the orientated and de-lidded raw plate bottom to the plate work position in the station. In one form of the present invention, the plate supply of the apparatus is formed by a plurality of removable cassettes, each cassette able to hold and then feed multiple raw plates to the plate transfer mechanism.

The plate transfer feed mechanism preferably includes an orientation mechanism, the orientation mechanism ideally providing for orientation of at least the bottom of the raw plate about a generally horizontal axis, together with de-lidding, before the de-lidded plate bottom is transferred into the plate work position. The orientation mechanism is preferably provided by a pair of opposed jaws, both of which are ideally provided by a retractable, vacuum-actuated gripping device, and one of which includes a pair of elongate prongs. When an inverted raw plate is gripped between the jaws, a held position is formed that defines a notional tube above and below the plate.

Preferably, the opposed jaws are mounted such that at least the bottom of the held plate can be rotated about an axis in one of the x or y directions such that the raw plate bottom can be orientated by 180 degrees about that axis to bring the raw plate bottom into its normal, upright orientation (referred to as its worked orientation). In this form, the raw plate bottom preferably rotates about a generally horizontal axis that intersects the notional tube.

Holding the raw plate bottom in this upright or worked orientation, the orientation mechanism is then preferably able to move to be located over the platform mentioned above, following which the upright and held raw plate bottom may be lowered onto the platform to be centralized and clamped thereby. In one form, all of these motions will occur in a single continuous movement, such that the raw plate bottom is slightly raised off the lid from its original orientation (with the lid being retained in its original orientation), and is then orientated into the worked orientation and lowered onto the platform in one motion. The raw plate bottom can then be left centralized and clamped upon the platform ready to be moved into the plate work position, also as mentioned above.

As will be appreciated, the reverse operation then moves the processed plate bottom out of the work plate position, where the lid can be re-applied by again rotating the plate bottom (again, preferably in a smooth continuous motion) into its original inverted orientation.

The orientation mechanism is more fully described in the present applicant's international patent application filed on 11 Jan. 2008 titled "Method and Apparatus for Orientating a Solid Growth Culture Medium Plate", claiming priority from Australian provisional patent application 20072007900145, the full content of which is hereby incorporated by reference.

The apparatus of the present invention preferably further includes a plate store capable of storing inoculated and streaked (processed) plates, again in an inverted orientation, together with a plate transfer store mechanism that is able to retrieve a processed plate bottom from the plate work position, re-orientate and re-lid the processed plate bottom, and transfer the processed plate to the plate store. In one form, the plate store is also formed by a plurality of removable cassettes, each cassette able to receive multiple processed plates from the plate transfer store mechanism and then store multiple processed plates.

With regard to the plate transfer store mechanism, it will be appreciated that the orientation mechanism referred to above, as a part of the plate transfer feed mechanism, will preferably additionally play the roles of retrieving the processed plate bottom from the plate work position, and re-orientating and re-lidding the processed plate bottom, these steps simply being the reverse of the steps described above for the orientation mechanism transferring the raw plate into the plate work position.

Therefore, the present invention also provides an apparatus for inoculating and streaking a solid growth culture medium in a plate, the streaking using a streaking applicator having a line of resiliently and flexibly supported spaced apart contact surfaces, the apparatus including:

(a) a plate supply capable of storing raw plates in an inverted orientation;
(b) a plate transfer feed mechanism capable of obtaining an inverted raw plate from the plate supply, orientating the raw plate such that its bottom is lowermost and its lid is removed, and transferring the orientated and de-lidded raw plate bottom to the plate work position in an inoculating and streaking station;
(c) the inoculating and streaking station including:
   the plate work position, having a notional action line fixed in two dimensions (x,y) in a predetermined position; and
   a plate rotation device for rotating a positioned plate to cause streaking;
(d) a sensor capable of locating the surface of the medium in a positioned plate to thereby determine for that plate, prior to inoculation and streaking of that plate, the third dimension (z) of the action line;
(e) an inoculating device capable of dispensing inoculum, along the action line, on the surface of the medium in the positioned plate;
(f) a streaking device capable of moving the streaking applicator such that its line of spaced apart contact surfaces contacts, along the action line, the surface of the medium in the positioned plate, prior to rotation of the positioned plate for streaking;
(g) a plate store capable of storing processed plates in an inverted orientation; and
(h) a plate transfer store mechanism capable of retrieving a processed plate bottom from the plate work position, re-orientating the processed plate bottom to its inverted orientation with its lid on, and transferring the processed plate to the plate store.

Additionally, the present invention also provides a method for inoculating and streaking a solid growth culture medium in a plate, the streaking using a streaking applicator having a line of resiliently and flexibly supported spaced apart contact surfaces, the method including the steps of:

(a) storing raw plates in an inverted orientation in a plate supply;
(b) obtaining an inverted raw plate from the plate supply, orientating the raw plate such that its bottom is lowermost and its lid is removed, and transferring the orientated and de-lidded raw plate bottom to a plate work position in an inoculating and streaking station, the plate work position having a notional action line fixed in two dimensions (x,y) in a predetermined position;

(c) locating the surface of the medium in the positioned plate to thereby determine for that plate, prior to inoculation and streaking of that plate, the third dimension (z) of the action line;
(d) dispensing inoculum along the action line on the surface of the medium in the positioned plate;
(e) moving the streaking applicator such that its line of spaced apart contact surfaces contacts, along the action line, the surface of the medium in the positioned plate;
(f) rotating the positioned plate in the plate work position for streaking; and
(g) retrieving the processed plate bottom from the plate work position, re-orientating the processed plate bottom to its inverted orientation with its lid on, and transferring the processed plate to a plate store.

It will also be appreciated that the abovementioned method and apparatus may be advantageously modified to also deal with "half-plates" (sometimes referred to as "bi-plates"). A half-plate is similar to the plates described above, but includes a physical barrier across the centre of the plate, such as an upstanding wall, that thus divides a circular plate into two semi-circular portions. Half-plates can be used in a manner such the two halves contain the same composition of solid growth culture medium, to be inoculated with the same or different types of samples, or such that the two halves contain different types of solid growth culture medium, again to be inoculated with the same or different types of samples (perhaps for comparative or experimental purposes). In some situations though, the use of half-plates will simply be to save space or time.

Where a half-plate is used in the method and apparatus of the present invention, it will be appreciated that various operations will be duplicated and some will be modified. For example, to use both halves of the half-plate in a situation where the same sample (from the same dispensing tip and using the same streaking applicator) is being inoculated onto both halves of a plate containing the same type of medium, the inoculation will occur twice and the streaking will occur twice (each time for only half a rotation of the plate, not a full rotation).

Thus, the plate would first be rotated a full turn to permit the sensor (mentioned above) to identify and locate the upstanding wall and then return the plate to a start position relative to a predetermined (in two dimensions only) notional action line. The first half would have its surface sensed to locate the action line in three dimensions, for it to then be inoculated along its action line. The plate would then be rotated to a second start position relative to another predetermined (in two dimensions only) notional action line.

The second half would then have its surface sensed to locate its action line in three dimensions, for it to then be inoculated along its action line, and then be streaked.

Turning now to a description of the supply of the microbiological sample to the apparatus and method of the present invention, the supply system preferably includes a plurality of sample containers (such as sample tubes) supported in multiple racks on a sample deck (the sample deck being accessible by an operator for sample rack input and removal). The system also preferably includes a two axis sample handling and transportation robot system that is able to manipulate the sample racks such that they are operatively accessible to the inoculation device. In terms of the samples themselves, they are likely to be in a liquid or semi-liquid form and might be: a biological fluid, such as blood, urine, plasma and cerebrospinal fluid; a liquid microbial culture; biological extracts; or environmental samples, such as water samples or soil wash samples.

Before turning to a detailed description of a preferred embodiment of the method and apparatus of the present invention, it will be appreciated by a skilled addressee that it will also be desirable to include within the apparatus a suitable form of barcode applicator and appropriate barcode readers. In a preferred form, barcode labels will have been applied (either manually or automatically) to each sample container to properly identify and record the presence and movement of each sample. Also, a barcode applicator will ideally be incorporated into the plate transfer store mechanism such that a suitable barcode label can be printed and applied to a processed plate as it is removed from the plate work position, in order to match a processed plate with the sample applied thereto and then to properly identify and record that processed plate.

BRIEF DESCRIPTION OF THE DRAWINGS

Having briefly described the general concepts involved with the present invention, a preferred embodiment will now be described that is in accordance with the present invention. However, it is to be understood that the following description is not to limit the generality of the above description.

In the drawings.

DESCRIPTION OF A PREFERRED EMBODIMENT

A preferred embodiment of the present invention will now be described in relation to the apparatus as illustrated (from the front and the rear) in FIGS. 1 and 2. These figures show unnecessary detail, and so will only be described to a depth of detail necessary to fully describe the invention as outlined above.

Further, the subsequent illustrations of FIGS. 3 to 7 each show different parts of the apparatus of FIGS. 1 and 2, and each will again will be described in sufficient detail to fully describe the invention as outlined above. In this respect, reference is again made to the present applicant's co-pending international patent applications filed contemporaneously with the present application, being patent applications titled "Method and Apparatus for Locating the Surface of Solid Growth Culture Media in a Plate", "A Streaking Applicator Cartridge and a System for Connecting Same to a Streaking Apparatus", and "Method and Apparatus for Orientating a Solid Growth Culture Medium Plate", the full contents of which are hereby incorporated by reference, for possibly fuller descriptions of some of these parts.

Figure 1:
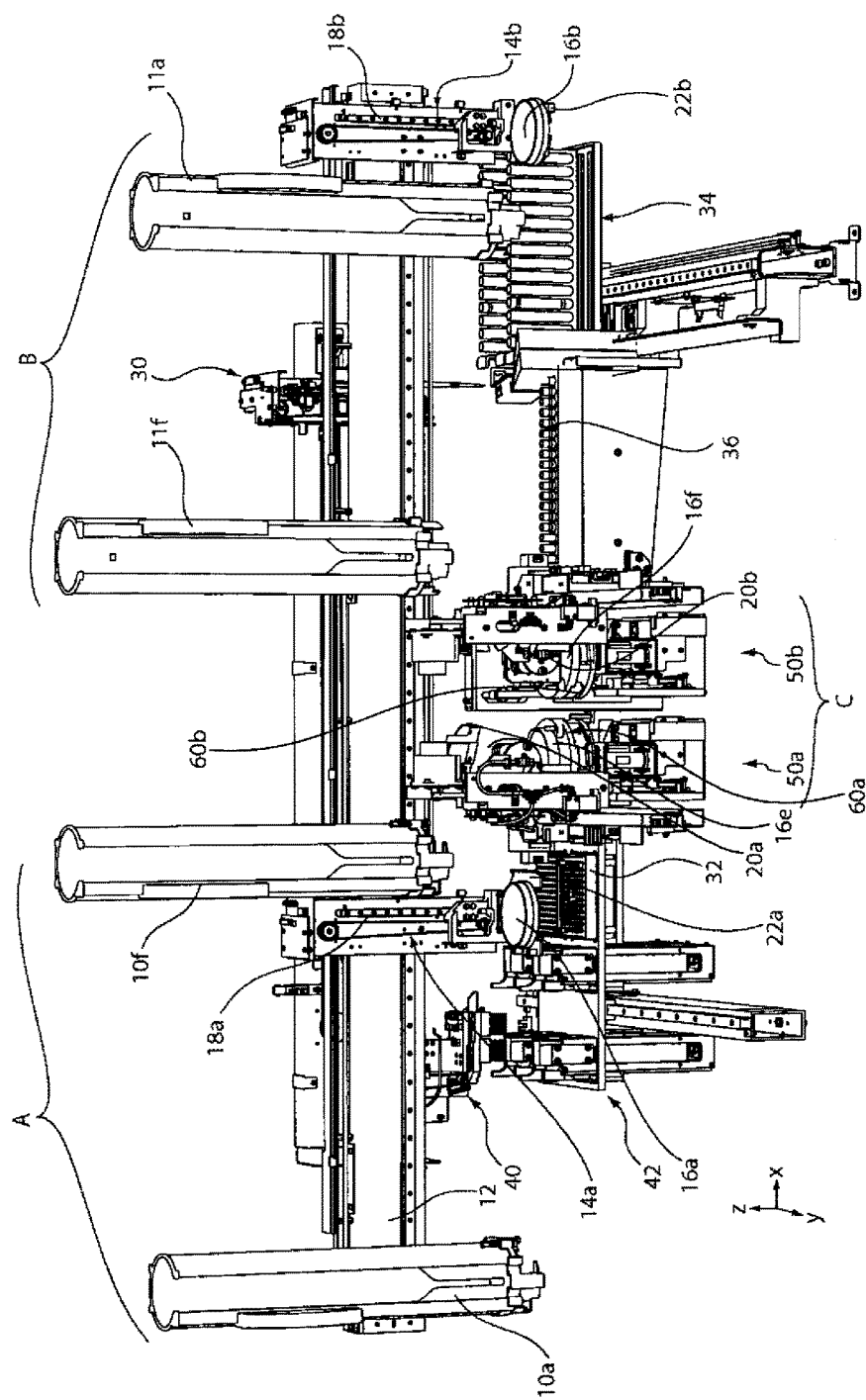
FIG. 1 is a perspective view from the front of an automated streaking apparatus according to a preferred embodiment of the present invention.
Figure 2:
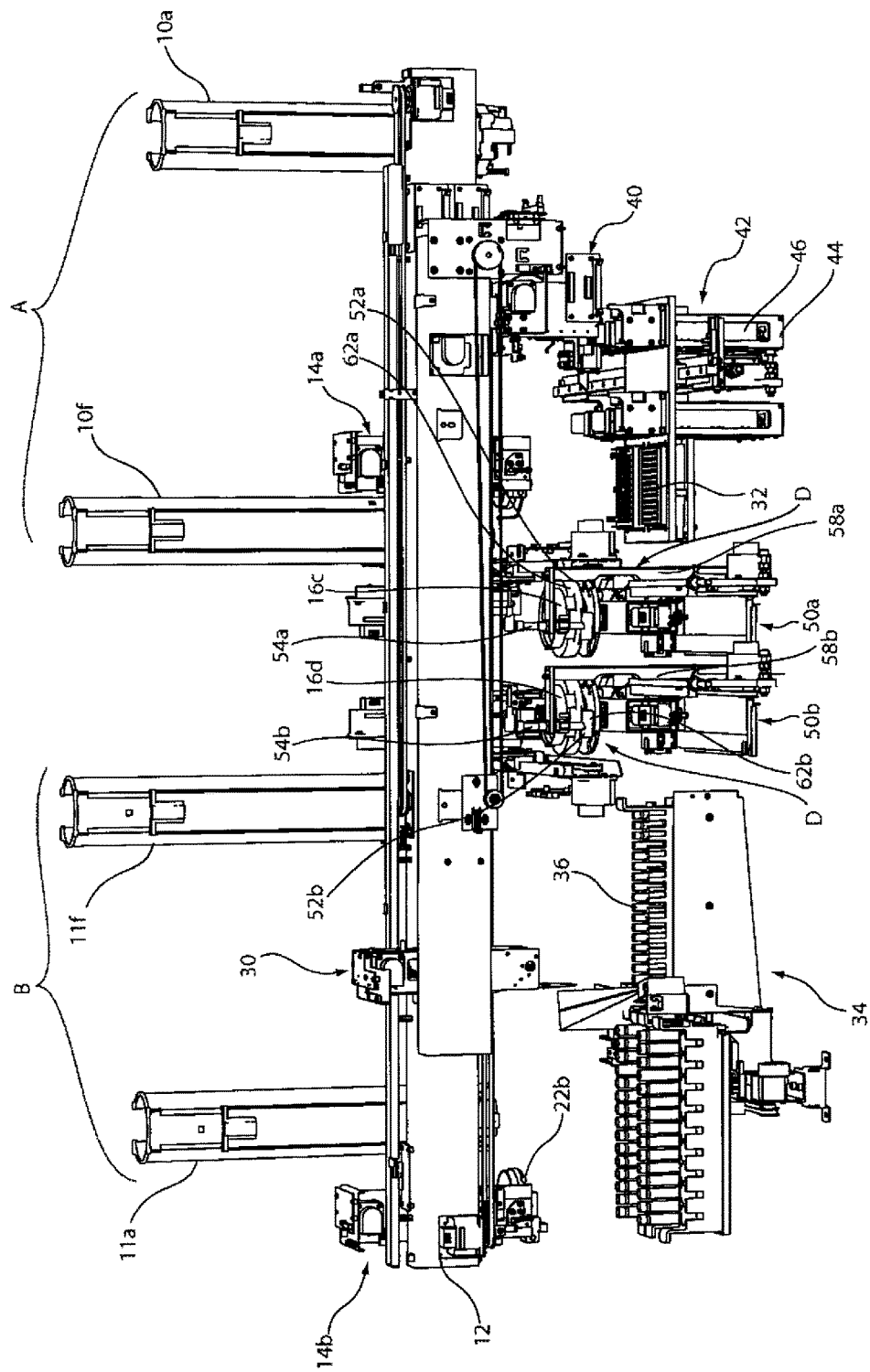
FIG. 2 is perspective view from the rear of the apparatus of FIG. 1.

Illustrated in FIGS. 1 and 2 is an apparatus for inoculating and streaking a solid growth culture medium in a plate. The apparatus includes a plate supply (generally indicated by the letter A) that includes a plurality of input plate cassettes 10 (only cassettes 10*a* and 10*f* are shown) supported on an upper frame (not shown) for the supply of raw plates to the apparatus, together with a plate store (generally indicated by the letter B) that includes a plurality of output plate cassettes 11 (only cassettes 11*a* and 11*f* are shown) also supported on the upper frame for the storage of processed plates from the apparatus. Also shown in FIG. 1 is an inoculation and streaking station, which is generally indicated by the letter C.

The plate supply A and the plate store B are supported by the upper frame so as to be in front of (in FIG. 1) a main gantry 12, along which various of the operative carriages of the apparatus will move, as will be explained below. The various parts of the inoculation and streaking station C are generally supported by a lower frame, which is also not shown in FIG. 1 or 2.

Shown in FIG. 1 operatively engaged for sliding movement along the main gantry 12 is a plate supply carriage 14*a* and a plate store carriage 14*b*, which form a part of a plate transfer feed mechanism and a plate transfer store mechanism (mentioned above) respectively. These carriages are both configured for movement along the main gantry 12 (in the x direction) to move a plate (16*a* or 16*b*) from the plate supply A to the inoculation and streaking station C and then to the plate store B. The carriages (14*a*,14*b*) are also configured to provide movement of a plate (16*a*,16*b*) along vertical guiderails (18*a*,18*b*) thereon to raise and/or lower such plate (16*a*,16*b*) in the z direction to or from the respective cassettes (10*a* to 10*f*, and 11*a* to 11*f*) and to or from either or both of the dual plate orientation mechanisms (20*a*, 20*b*).

In this respect, it can be seen that each of the carriages includes a plate support tray (22*a*,22*b*) upon which the plates 16*a*,16*b* rest in transit, the plate support trays (22*a*,22*b*) being suitable mounted to their respective carriages for the movement described above. It can also be seen that, in this embodiment of the invention, the plates are supplied and stored in their respective cassettes in an inverted orientation, such that their bottoms are uppermost and their lids are lowermost.

Also configured for movement along the main gantry 12 are an inoculating device 30 and a streaking device 40, in this embodiment again both mounted upon a suitable carriage for movement along the main gantry in the x direction. The inoculation device 30 is a pipette robot system controlled so as to be able to access supply 32 of dispensing tips and a sample supply system 34 that includes a number of supply tubes 36, and also access a plate work position (one such position shown in FIG. 2 by the letter D) for inoculation purposes. The streaking device 40 is a streaking robot system controlled so as to be able to access a streaking applicator supply 42 that, in this embodiment, includes four applicator supply cartridges 46 received in four corresponding cartridge holders 44.

Before turning to a more detailed description of some of these parts of this embodiment of the apparatus of the present invention, the last general aspect of FIGS. 1 and 2 to be described is the inoculation and streaking station C. In this embodiment, the inoculation and streaking station C of the apparatus includes dual plate work positions D and dual rotation devices (52*a*,52*b*) for the streaking of dual plates (being indicated by reference numerals 16*c*,16*d* evident in FIG. 2 in the dual plate work positions D), and dual plate orientation mechanisms (20*a*,20*b*), the location of which is all generally indicated in FIGS. 1 and 2 by the reference numerals 50*a* and 50*b*. While FIG. 2 generally shows de-lidded plates 16*c*,16*d* in the plate work positions D underneath dual sensors (54*a*,54*b*), FIG. 1 shows dual plates (16*e*,16*f*) being orientated and de-lidded by the dual orientation mechanisms (20*a*,20*b*). It will of course be appreciated that such a dual configuration is not essential for an apparatus in accordance with the present invention, and that single such stations and devices could be used. Indeed, an apparatus that includes three or four or more such stations and devices is also envisaged.

It can also be seen that, in this embodiment, the inoculating and streaking station C is the general location within the apparatus where the main functions of the apparatus occur, which location is generally centered around the plate work positions D. It can also be seen that, in this embodiment, the plate work positions D are themselves identified by (and in essence defined by) the physical location in the apparatus of the sensors (54*a*,54*b*), the sensors (54*a*,54*b*) being rigidly mounted to respective sensor mounting frames (58*a*,58*b*). Therefore, the apparatus also includes dual plate platforms for supporting a plate, although the combination of FIGS. 1 and 2 shows four such platforms, being the dual platforms (60*a*,60*b*) in the positions shown in FIG. 1, and the platforms (62*a*,62*b*) shown in FIG. 2. In this respect, these figures each show two platforms (in different positions) simply for the sake of description—the apparatus of the embodiment will actually only include two such platforms.

Figure 3A:
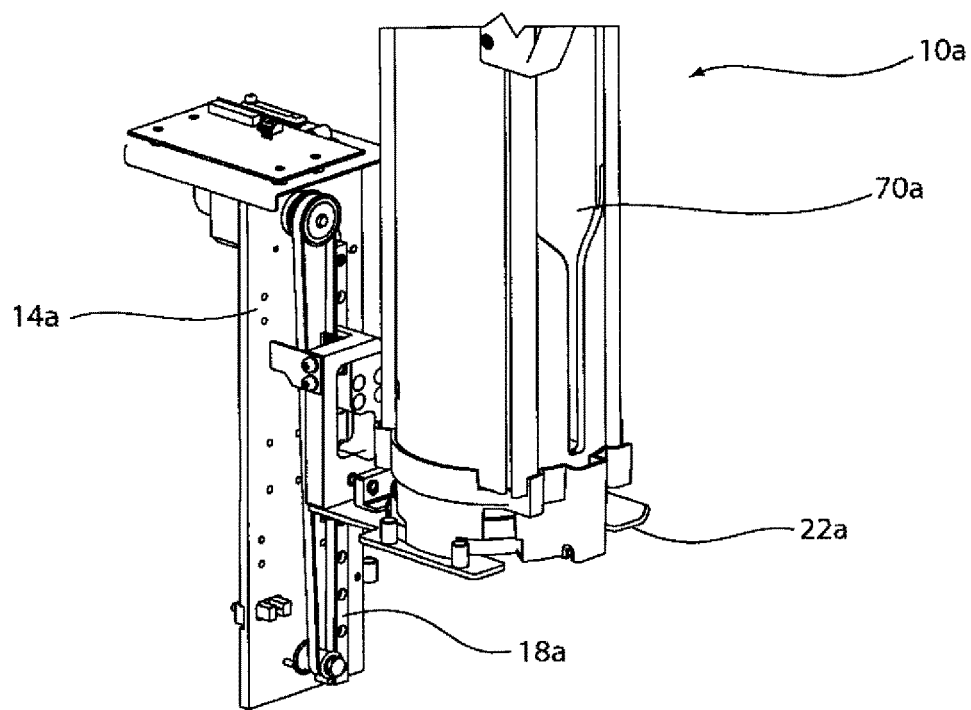
FIGS. 3a and 3b are perspective partial views of preferred forms of plate supply and plate store for the apparatus of FIG. 1.
Figure 3B:
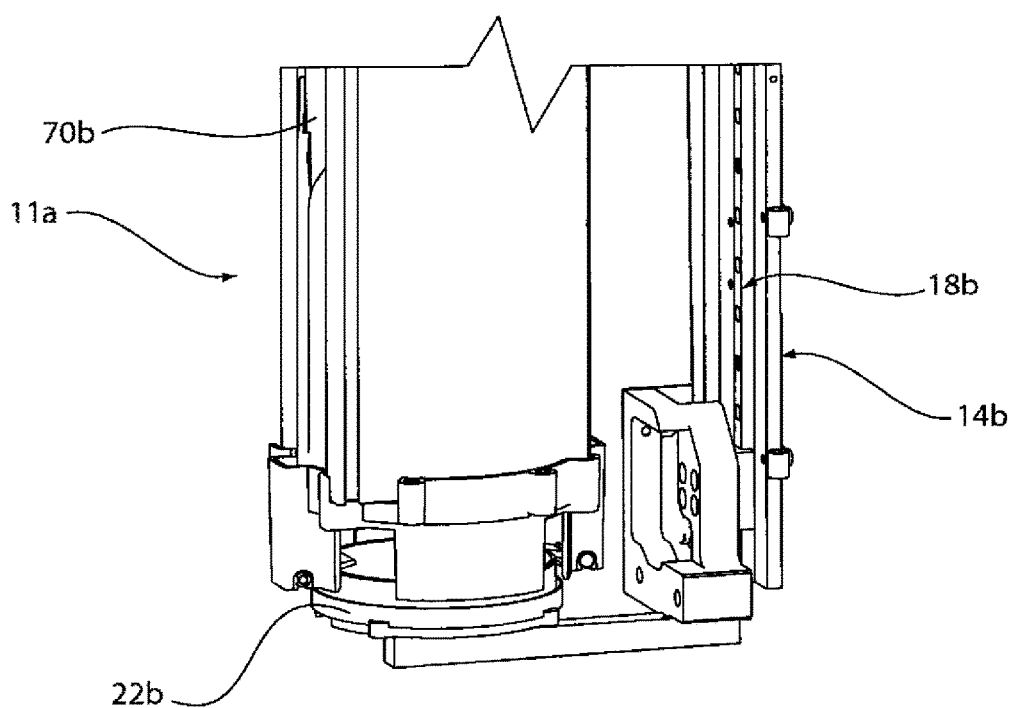

Turning now to a more detailed description of some of the parts of the apparatus illustrated in FIGS. 1 and 2, reference is firstly made to FIGS. 3*a* and 3*b* that show examples of suitable removable cassettes (10*a*,11*a*) for use in the plate supply A and the plate store B. Each cassette (10*a*,11*a*) is able to hold multiple plates within their inner chambers (70*a*,70*b*)—in the case of cassette 10*a* for the purpose of providing raw plates to the apparatus for subsequent processing, and in the case of cassette 11*a* for the purpose of storing processed plates following inoculation and streaking in the apparatus. As can be seen, each of the cassettes (10*a*,11*a*) also interacts with its respective carriage (14*a*, 14*b*) to capture a plate, from below, on the respective trays (22*a*, 22*b*) due to respective internal engaging and plate release/lock means (not shown).

Figure 4A:
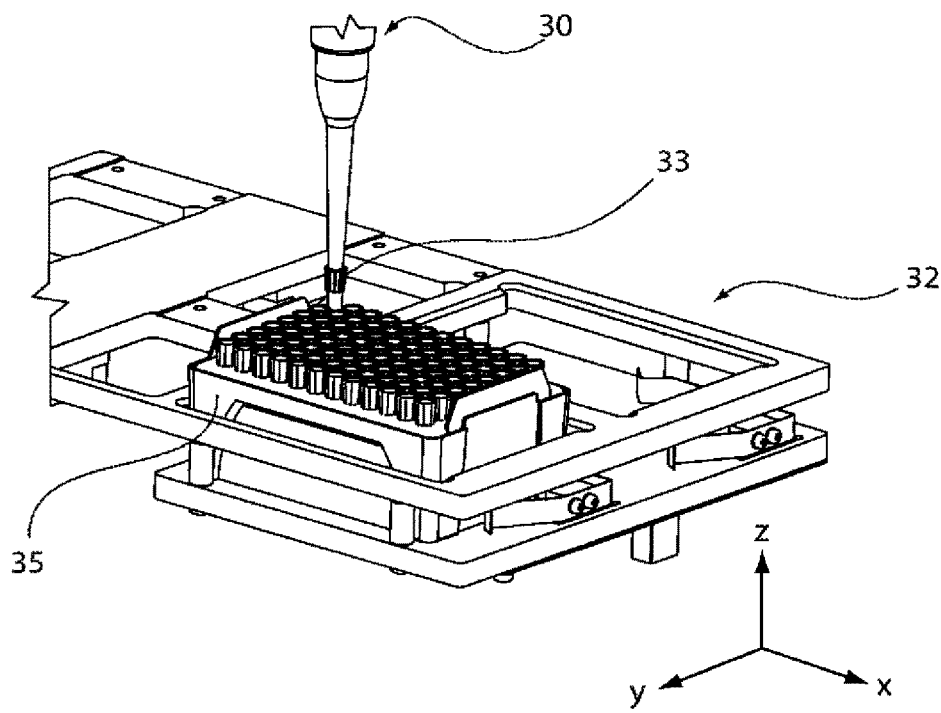
FIGS. 4a and 4b are perspective partial views of preferred forms of pipette tip and sample supply systems for use with an inoculating device for the apparatus of FIG. 1.
Figure 4B:
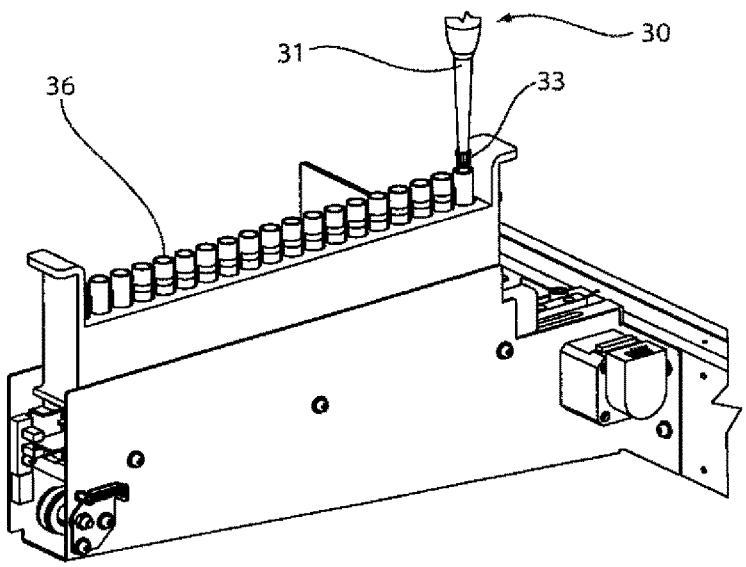

In relation to FIGS. 4*a* and 4*b*, as mentioned above, the inoculating device 30 of the apparatus of the present invention can be any device that is able to obtain and hold a biological sample, generally in a liquid form, and transfer that sample to the surface of a medium in a positioned plate. In this embodiment, the inoculating device 30 is pipette device 31 mounted to a robot system (not shown) so as to be movable in the z direction, as well as the x,y directions along the main gantry 12 as mentioned above.

The pipette device 31 includes a disposable dispensing tip 33 releasably secured thereto in a manner that permits easy disposal of the tip 33 once inoculation has been affected. The pipette device 31 is programmable for various inoculum volumes, and includes a positional height (z direction) referencing system (not shown) capable of determining in three dimensional space the height of the location of the dispensing tip 33 relative to the datum level and reference points of a platform (60*a*,60*b*,62*a*,62*b*) as will be described below, and of course relative to the notional action line mentioned above.

The pipette robot system is able to move the pipette device 31 to access a dispensing tip supply 32, which includes a rack 35 of dispensing tips 33, the biological sample station 34, which includes a rack of sample containers such as sample tubes 36, the plate work position D in the inoculating and streaking station C, and also a tip waste disposal chute (not shown), whilst also including suitable tip securing means that allows for a tip 33 to be secured, used to obtain and hold sample, dispense sample, and then dispose of the used tip 33.

Figure 5:
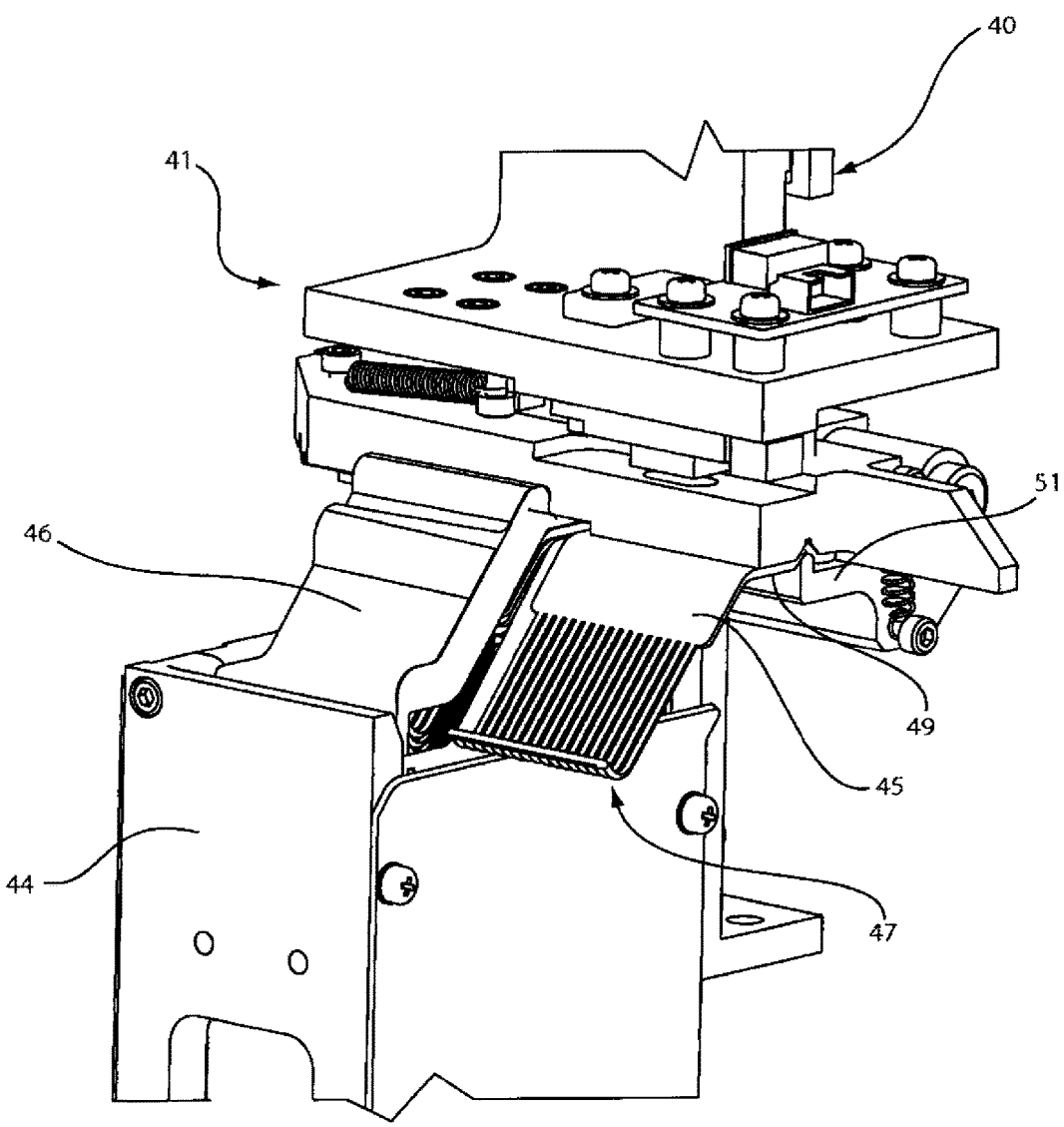
FIG. 5 is a perspective view of a preferred form of streaking device obtaining a streaking applicator for use with the apparatus of FIG. 1.

Turning to FIG. 5, the streaking device 40 is a separate device to the inoculating device 30, and in this embodiment is provided by its own robot system that includes an applicator handling head 41 suitable to obtain (from a supply cartridge 46 in a cartridge holder 44) and hold a streaking applicator 45, and then transfer that applicator 45 to a plate work position D and adjacent a positioned plate (generally all in the x,y plane). The applicator handling head 41 then must be able to move the applicator 45 in the z direction to locate the line of contact surfaces of the applicator 45 (here represented as being located along the lowermost curved portion 47 of the applicator 45, along the notional action line (and thus upon/within the inoculum on the surface of the medium in the positioned plate) as mentioned above and as will be better described below in relation to this embodiment.

As mentioned above, streaking applicators preferred for use with the apparatus of the present invention are the streaking applicators generally described in the abovementioned international patent publication WO2005/071055 (Medvet Science Pty Ltd) titled "Microbial Streaking Device" (licensed to the present applicant), the full content of which is herein incorporated by reference. These streaking applicators can be said to have a generally flat rectangular form, albeit with two major inclined portions that together form a very shallow inverted v-shaped body. An upper portion 49 of the body provides a mounting portion and the lower curved portion 47 of the body provides the line of spaced apart contact surfaces, there being a resilient and flexible support member therebetween, which in the form illustrated in FIG. 5 is made up of a plurality of elongate members.

The applicator handling head 41 of the streaking robot system thus includes an openable clamping member 51 that is able to grasp and clamp the mounting portion 49 of the applicator 45 mentioned above, the applicator 45 being provided in a supply cartridge 46 held in a cartridge holder 44, both of the type generally described in the present applicant's concurrently filed international patent application referred to above and titled "A Streaking Applicator Cartridge and a System for Connecting Same to a Streaking Apparatus".

The openable clamping member 51 of the streaking robot system preferably includes a release catch (not shown) which is able to interact with a fixed eject pin (not shown) located near an applicator disposal chute (not shown), such that engagement of the pin with the latch causes the clamping member to release the applicator and allow it to fall into the applicator disposal chute.

Figure 6A:
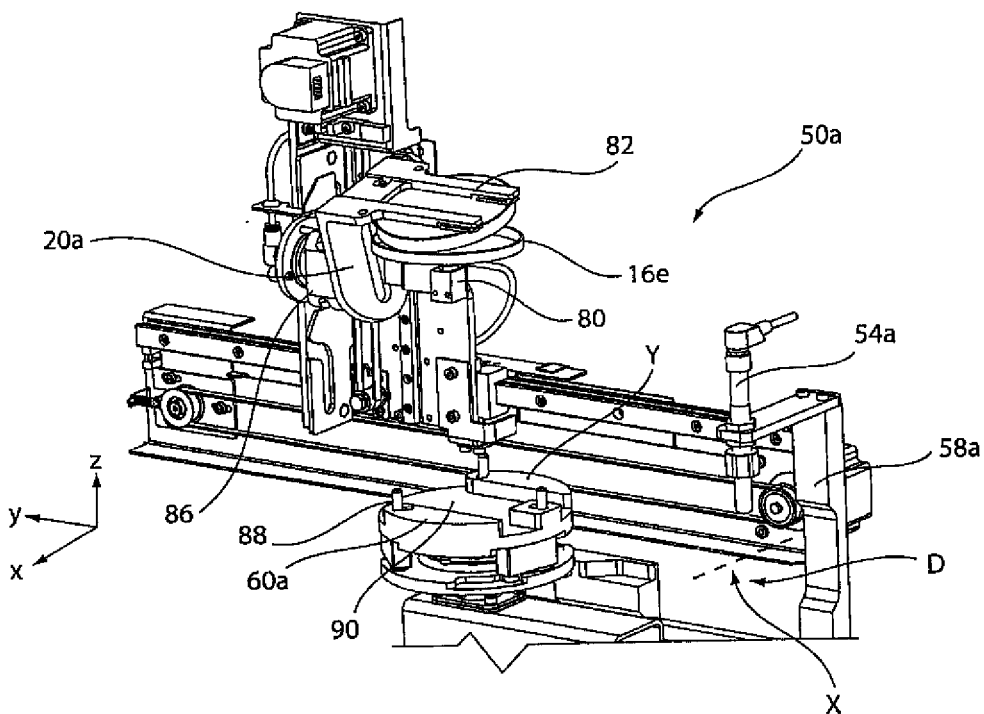
FIGS. 6a and 6b are perspective partial views of a preferred form of orientation device for use with the apparatus of FIG. 1.
Figure 6B:
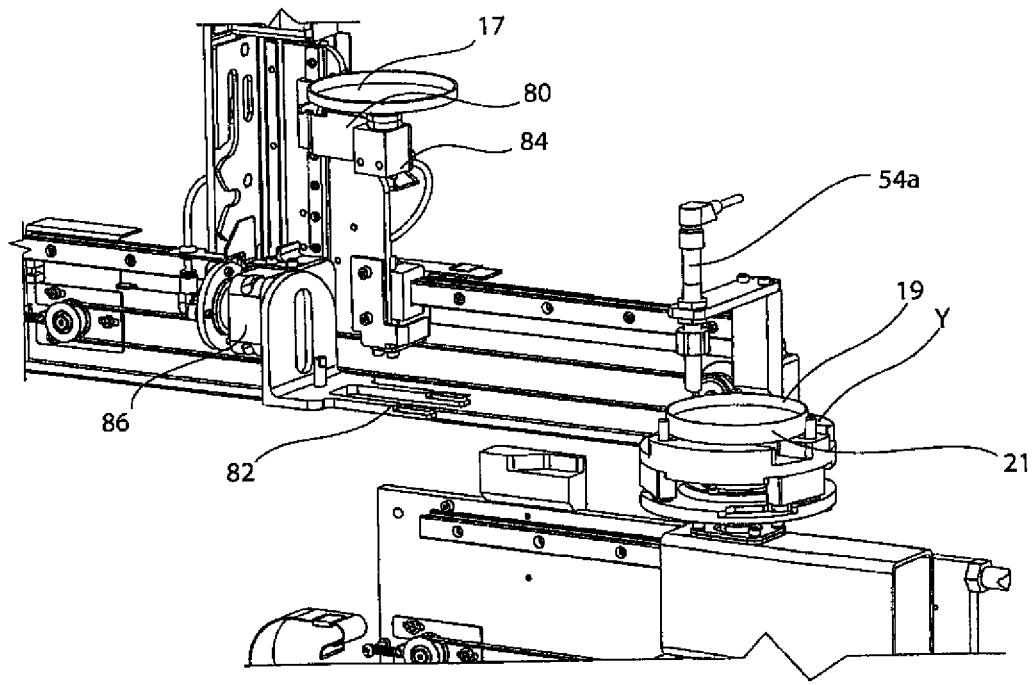

In relation to FIGS. 6a and 6b, the apparatus of this embodiment includes dual orientation mechanisms (loosely identified in FIGS. 1 and 2 by the reference numerals 50a and 50b) that are able to rotate plates (or at least plate bottoms) from a held position in an original orientation to a worked orientation. FIGS. 6a and 6b show more detail of one of these mechanisms 50a.

FIG. 6a shows the mechanism 50a commencing its operation to orientate and de-lid the plate 16e for subsequent transfer of the plate bottom to the plate work position D adjacent the sensor 54a, while FIG. 6b shows the same plate 16e orientated in the worked orientation, de-lidded, and transferred such that the bottom of the plate 16e is in the plate work position D.

The plate 16e has a lid 17 and a bottom 19 and, in this embodiment, is a circular plate that has a single perimetric sidewall 21. The orientation mechanism 20a includes opposed jaws (being a lower jaw 80 and an upper jaw 82 when viewed in FIG. 6a) able to receive and hold the plate 16e therebetween. One of the jaws (in this case the lower jaw 80) is a retractable, vacuum-actuated lid-gripping device 84, the other (the upper jaw 82) is a retractable pair of elongate prongs spaced apart by a distance no larger than the diameter of the bottom 19 of the plate 16e, the upper jaw 82 also including a vacuum-actuated plate-bottom gripping device in the form of respective vacuum-actuated suction cups.

When initially placed between the jaws (80,82), the plate 16e is held therebetween in a position that is thus defined as a "held position". The held position defines a notional tube above and below the plate 16e, the notional tube being a continuation of a partial circular tube formed by the sidewall 21 of the plate 16e, which continues indefinitely above and below the plate 16e.

The orientation mechanism 20a includes a jaw support member 86 upon which the upper jaw 82 is mounted. The upper jaw 82 is mounted on the support member 86 such that the plate 16e rotates about a generally horizontal axis that intersects the notional tube to orientate the plate bottom 19 from the original orientation to the worked orientation. The jaw support member 86 is also movable generally vertically (in the y direction) such that the plate bottom 19, during orientation, can then be lowered onto the plate platform 60a from above (still within the notional tube) such that the plate bottom 19 is moved downwardly in a smoothly continuous motion to engage with a plate clamping member 88, with the prongs of the jaw 82 being loosely received within a cooperatively shaped channel 90 of the platform 60a such that they are not clamped when the plate 16e is clamped.

In this embodiment, the plate clamping member 88 is in the form of three movable lugs operated by a camming device (not shown), which lugs are preferably also able to function as a plate centralizing means for centralizing the position of the plate on the platform 60a. This can be useful for subsequent operations with the plate 16e.

Then, in operation, and once the plate bottom 19 is clamped to and centralized in the platform 88, the clamped bottom 19 can then be moved away from the prongs horizontally (in the y direction), and independently of the orientation mechanism 20a, away from the notional tube and into a plate work position D, where easy access to the medium in the plate 16e can be provided.

As will be appreciated, the reverse operation then moves the platform 60a, with the clamped bottom 19 of the plate 16e (after processing in the plate work position D and with no lid 17), out of the plate work position D within the notional tube of the held position, where the prongs are again loosely received within the channel 90 of the platform 60a by the plate clamping member 88 of the platform 60a (and are arranged under the plate bottom 19). The lid 17 can then be re-applied to the plate bottom 19 by slightly raising and then rotating the plate bottom 19 back up and around the lid 17 to be returned to its original orientation.

The orientation mechanism 50a is more fully described in the present applicant's concurrently filed international patent application referred to above and titled "Method and Apparatus for Orientating a Solid Growth Culture Medium Plate".

Figure 7A:
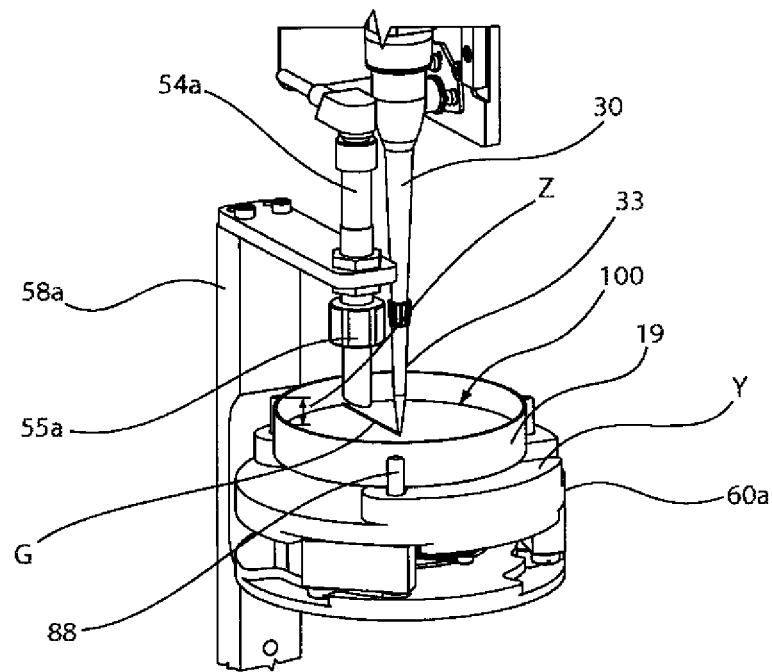
FIGS. 7a and 7b are perspective partial views of a preferred configuration of plate work position during inoculation and streaking by the apparatus of FIG. 1.
Figure 7B:
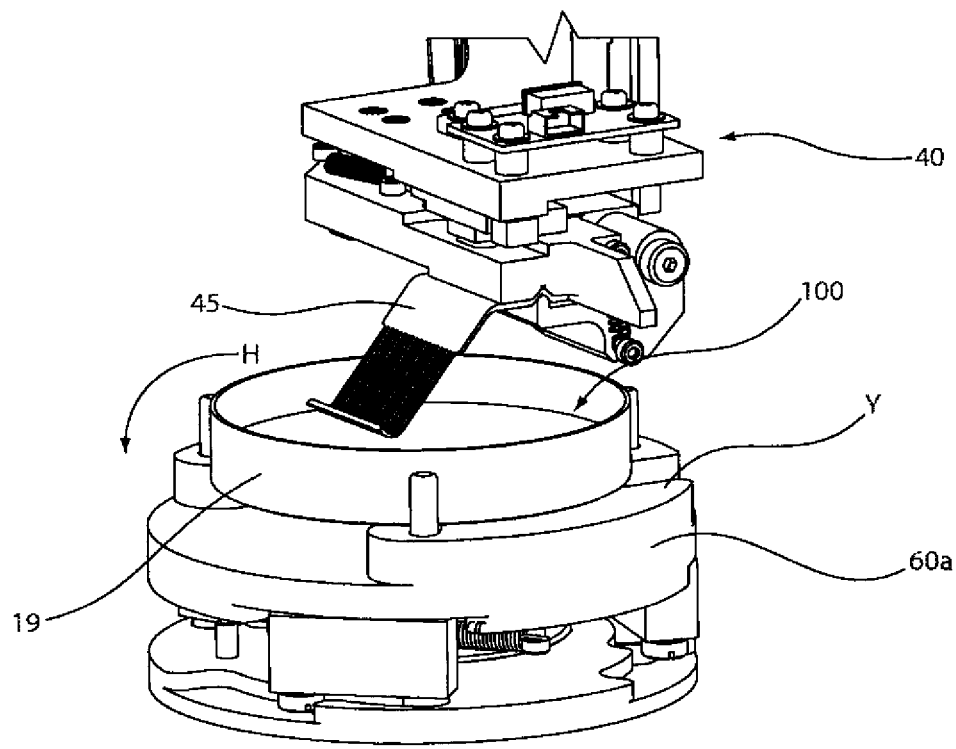

Finally with reference to FIGS. 7a and 7b, reference can be made to operations that occur in the plate work position D identified earlier in FIGS. 1 and 2. With reference to FIG. 7a, illustrated is a plate platform 60a with a plate bottom 19 in a centralized and clamped position in the plate work position D. As mentioned above, the plate platform 60a includes a plate clamping member 32 in the form of three movable lugs operated by a camming device (not shown), which lugs are preferably also able to function as a plate centralizing means for centralizing the position of the plate bottom 19 on the platform 60a.

The plate work position D includes a notional action line X (shown by a broken line in FIG. 6a) fixed in two dimensions (x,y) in a predetermined position, together with a datum level Y, which in FIG. 6a is shown as a surface upon the plate platform 60a (eventually to be located within the plate work position D as per the illustration in FIG. 7a). In the present invention, the notional action line X is fixed in two dimensions (x,y) in a predetermined position. Again as mentioned above, the action line is herein referred to as being a "notional" action line given that it will not be a visible action line and also will not have a determined position in three dimensional space until the height of the surface 100 of the medium in the plate bottom 19 is determined.

FIG. 7a shows an apparatus for locating the surface 100 in the plate bottom 19, and includes the sensor 54a. In this embodiment of the invention, the notional action line X is of course fixed in two dimensions (x,y) in its predetermined position, and the plate work position D includes a datum level Y, which is the uppermost surface upon the plate platform 60a.

The sensor 54a includes an ultrasonic sensing device 55a having an ultrasonic beam focusing element that is capable of providing a focused beam on the surface 100, preferably within a sensing region (not identified in FIG. 7a) that is central to the notional action line X. The sensor 54a is rigidly mounted via a sensor support arm 58a, thereby defining the general location of the plate work position D. In this form, the sensor 54a is ideally mounted so that it is above the plate work position D and is operatively adjacent the plate bottom 19 held immediately therebelow in the plate platform 60a, the plate bottom 19 having its surface 100 open upwardly.

The preferred operation of the sensor is thus for it to sense the surface 100 and measure the distance to the surface 100. Then, the measured distance is referenced to the datum level Y to determine a surface positional reference relative to the datum level Y in one dimension (z) for the surface 100 in the plate bottom 19. In this manner, it will be appreciated that the surface 100 can thus be located in at least the z dimension by virtue of the determination of this surface positional reference. This effectively determines the height of the medium in the plate bottom 19, at least with reference to that datum level Y. In this respect, and as can be seen in the figures, the datum level Y is a surface that forms a part of the plate platform 60a upon which the plate is clamped and supported.

Therefore, in this embodiment, the determination of the surface positional reference effectively determines the height of the medium with reference to the plate platform 60a upon which it rests.

This surface positional reference can then be used, together with the notional action line X (shown in earlier figures) to determine the line G in three dimensions (x,y,z) that is representative of a line across the surface 100 in the positioned plate.

As with other parts of the apparatus of the present invention, the sensor 54a is more fully described in the present applicant's concurrently filed international patent application referred to above and titled "Method and Apparatus for Locating the Surface of Solid Growth Culture Media in a Plate".

The notional three dimensional action line that is represented by the line G across the surface 100 of the medium in the plate bottom 19 will be specific to the medium in that plate bottom 19 only, and may be (and is actually likely to be) a different three dimensional action line compared to the surface of the next plate processed in the plate work position D. In the preferred form illustrated here, the predetermined (x,y) position of the notional action line X is, with reference to the circular plate bottom 19, located such that the notional action line X will be a radial line for a circular plate, which then means that the line G which represents the action line in three dimensions (x,y,z) will be also.

In this form, and as shown in FIG. 7a, having utilized the sensor to determine the proper position of the three dimensional action line, represented by the line G in FIG. 7a, for media in a given positioned plate in three dimensional space, during inoculation of the surface 100 of the medium in the apparatus of the present invention by the inoculating device 30, the biological sample can be deposited on the surface 100 of the medium along the radial line G in a manner such that the dispensing tip 33 is not located too far away from the surface 100 nor too close to the surface 100. In this respect, it will be appreciated that a reference throughout this specification to a biological sample being dispensed "along" a line (or there being inoculation "along" a line), is to include a variety of forms of depositing/inoculation. For example, a sample may be deposited continuously along the full length of the line, or may be deposited semi-continuously along the line, such as may be provided by a series of discrete deposits in the form of dots and/or dashes as required.

Now referring to FIG. 7b, the apparatus of the present invention is then able to move the streaking device 40 such that the line of spaced apart contact surfaces of a streaking applicator 45 contacts, again along that line G, at least the inoculum (and preferably also the surface 100 of the medium itself) on the surface 100 of the medium in the plate bottom 19, with a predetermined contact pressure that is suitable for the particular streaking applicator 45 being used and also for the composition of the inoculum and of the particular solid growth medium being used, such that the inoculum is spread when the platform 60a is rotated in the direction of arrow H, such that the streaking applicator 45 does not undesirably gouge the surface of the medium.

Certain embodiments or configurations of the present invention may be described by the following aspects:

1. An apparatus for inoculating and streaking a medium in a plate, the streaking using a streaking applicator having a line of resiliently and flexibly supported spaced apart contact surfaces, the apparatus including:
   (a) an inoculating and streaking station including:
      a plate work position having a notional action line fixed in two dimensions (x,y) in a predetermined position; and
      a plate rotation device for rotating a positioned plate to cause streaking;

(b) a sensor capable of locating the surface of the medium in a positioned plate to thereby determine for that plate, prior to inoculation and streaking, the third dimension (z) of the action line;

(c) an inoculating device capable of dispensing inoculum, along the action line, on the surface of the medium in the positioned plate; and (d) a streaking device capable of moving the streaking applicator such that its line of spaced apart contact surfaces contacts, along the action line, the surface of the medium in the positioned plate, prior to rotation of the positioned plate for streaking.

2. An apparatus according to aspect 1, including a platform for supporting a plate, the platform able to be moved into and out of the plate work position from a plate loading position, such that the plate supported in the platform becomes positioned in the plate work position operatively adjacent the sensor.

3. An apparatus according to aspect 2, wherein the platform includes a plate centering mechanism for constant central positioning of a plate upon the platform.

4. An apparatus according to aspect 3, wherein the plate centering mechanism includes a plate clamping function.

5. An apparatus according to any one of aspects 2 to 4, wherein the platform provides a datum level.

6. An apparatus according to any one of aspects 2 to 5, wherein the plate rotation device is provided in association with the platform, the rotation device including a home flag which allows for the return of a rotated plate to a starting position.

7. An apparatus according to any one of aspects 1 to 6, wherein the plate work position is provided by the physical location in the apparatus of the sensor, the sensor being rigidly mounted to a main frame.

8. An apparatus according to any one of aspects 1 to 7, wherein the sensor is an ultrasonic sensing device having an ultrasonic beam focusing element to provide a focused beam on the surface of the medium.

9. An apparatus according to aspect 8, wherein the beam is focused within a usable area that is central to the action line in its predetermined (x,y) position.

10. An apparatus according to aspect 8 or aspect 9, when appended via claim 5, wherein the sensor senses the surface and measures the distance to the surface, then referencing the measured distance to the datum level to determine a surface positional reference relative to the datum level in one dimension (z) for the surface, and uses the surface positional reference and the two fixed dimensions of the notional action line to determine the notional action line in three dimensions (x,y,z).

11. An apparatus according to any one of aspects 1 to 10, wherein the inoculating device includes a pipette device mounted to a robot system so as to be movable in the z direction and at least one of the x,y directions.

12. An apparatus according to aspect 11, wherein the pipette device includes a disposable tip releasably secured to a pipette body.

13. An apparatus according to aspect 11 or aspect 12, when appended via claim 5, wherein the pipette device is programmable for various inoculum volumes, and includes a positional height (z direction) referencing system relative to the locating datum surface of the platform.

14. An apparatus according to any one of aspects 1 to 13, wherein the streaking device includes a robot system that includes an applicator handling head suitable to obtain and hold a streaking applicator, and then transfer that applicator to the plate work position adjacent a positioned plate.

15. An apparatus according to aspect 14, wherein the applicator handling head is able to move the applicator in the z direction to locate the line of contact surfaces of the applicator along the notional action line on the surface of the medium in a positioned plate.

16. An apparatus according to aspect 14 or aspect 15, wherein the applicator handling head of the streaking robot system includes an openable clamping member that is able to grasp and clamp a mounting portion of a streaking applicator.

17. An apparatus according to aspect 16, wherein the openable clamping member of the streaking robot system includes a release catch which is able to interact with a fixed eject pin located near an applicator disposal chute, such that engagement of the pin with the latch causes the clamping member to release the applicator and allow it to fall into the applicator disposal chute.

18. An apparatus according to aspect 1 substantially as herein described in relation to the accompanying Figures.

19. A method for inoculating and streaking a medium in a plate, the streaking using a streaking applicator having a line of resiliently and flexibly supported spaced apart contact surfaces, the method including the steps of:

(a) placing a plate in a plate work position in an inoculating and streaking station, the plate work position having a notional action line fixed in two dimensions (x,y) in a predetermined position;

(b) locating the surface of the medium in the positioned plate to thereby determine for that plate, prior to inoculation and streaking of that plate, the third dimension (z) of the action line;

(c) dispensing inoculum along the action line on the surface of the medium in the positioned plate;

(d) moving the streaking applicator such that its line of spaced apart contact surfaces contacts, along the action line, the surface of the medium in the positioned plate; and (e) rotating the positioned plate in the plate work position for streaking 20. A method according to aspect 19, wherein the plate work position also has a datum level.

21. A method according to aspect 20, the method including the use of a sensor to sense the surface and measure the distance to the surface, referencing the measured distance to the datum level to determine a surface positional reference relative to the datum level in one dimension (z) for the surface.

22. A method according to aspect 21, including using the surface positional reference and the two fixed dimensions of the notional action line to determine the notional action line in three dimensions (x,y,z), the notional action line being a line representative of the surface of the medium.

23. A method according to aspect 22, including dispensing inoculum along the representative line across the surface of the medium in the positioned plate.

24. A method according to aspect 19, substantially as herein described in relation to the accompanying Figures.

25. An apparatus for inoculating and streaking a solid growth culture medium in a plate, the streaking using a streaking applicator having a line of resiliently and flexibly supported spaced apart contact surfaces, the apparatus including:

(a) a plate supply capable of storing raw plates in an inverted orientation;

(b) a plate transfer feed mechanism capable of obtaining an inverted raw plate from the plate supply, orientating the raw plate such that its bottom is lowermost and its lid is removed, and transferring the orientated and de-lidded raw plate to the plate work position in an inoculating and streaking station;

(c) the inoculating and streaking station including:
the plate work position, having a notional action line fixed in two dimensions (x,y) in a predetermined position; and
a plate rotation device for rotating a positioned plate to cause streaking;

(d) a sensor capable of locating the surface height of the medium in a positioned plate to thereby determine for that plate, prior to inoculation and streaking of that plate, the third dimension (z) of the action line;

(e) an inoculating device capable of dispensing inoculum, along the action line, on the surface of the medium in the positioned plate;

(f) a streaking device capable of moving the streaking applicator such that its line of spaced apart contact surfaces contacts, along the action line, the surface of the medium in the positioned plate, prior to rotation of the positioned plate for streaking;

(g) a plate store capable of storing processed plates in an inverted orientation; and (h) a plate transfer store mechanism capable of retrieving a processed plate from the plate work position, re-orientating the processed plate to its inverted orientation with its lid on, and transferring the processed plate to the plate store.

26. An apparatus according to aspect 25, wherein the plate supply is formed by a plurality of removable cassettes, each cassette able to hold and then feed multiple raw plates to the plate transfer mechanism.

27. An apparatus according to aspect 25 or aspect 26, wherein the plate transfer feed mechanism includes an orientation mechanism, the orientation mechanism providing for orientation of at least the raw plate bottom about a generally horizontal axis, before the de-lidded raw plate is transferred into the plate work position.

28. An apparatus according to aspect 27, wherein the orientation mechanism is provided by a pair of opposed plate receiving jaws.

29. An apparatus according to aspect 28, wherein at least one of the jaws is provided by a retractable, vacuum-actuated device, and one is provided by a pair of elongate prongs.

30. An apparatus according to aspect 29, wherein at least one of the jaws is mounted for rotation about an axis in one of the x or y directions such that the inverted raw plate held between the jaws can have at least its bottom orientated by 180 degrees about that axis to bring the plate bottom into its upright orientation.

31. An apparatus according to aspect 30, wherein the orientation mechanism is then able to move to be located over a platform, following which the upright and held raw plate bottom may be lowered onto the platform.

32. An apparatus according to aspect 31, wherein the raw plate is left centralized and clamped upon the platform ready to be moved into the plate work position.

33. An apparatus according to any one of aspects 25 to 32, wherein the plate store is formed by a plurality of removable cassettes, each cassette able to receive multiple processed plates from the plate transfer store mechanism and then store multiple processed plates.

34. An apparatus according to any one of aspects 27 to 32, wherein the orientation mechanism forms a part of the plate transfer store mechanism, and functions to retrieve the processed plate bottom from the plate work position, and re-orientate the processed plate bottom to its original inverted orientation with its lid on.

35. An apparatus according to aspect 25, substantially as herein described in relation to the accompanying Figures.

36. A method for inoculating and streaking a solid growth culture medium in a plate, the streaking using a streaking applicator having a line of resiliently and flexibly supported spaced apart contact surfaces, the method including the steps of:

(a) storing raw plates in an inverted orientation in a plate supply;

(b) obtaining an inverted raw plate from the plate supply, orientating the raw plate such that its bottom is lowermost and its lid is off, and transferring the orientated and de-lidded raw plate to a plate work position in an inoculating and streaking station, the plate work position having a notional action line fixed in two dimensions (x,y) in a predetermined position;

(c) locating the surface of the medium in the positioned plate to thereby determine for that plate, prior to inoculation and streaking of that plate, the third dimension (z) of the action line;

(d) dispensing inoculum along the action line on the surface of the medium in the positioned plate;

(e) moving the streaking applicator such that its line of spaced apart contact surfaces contacts, along the action line, the surface of the medium in the positioned plate;

(f) rotating the positioned plate in the plate work position for streaking; and (g) retrieving the processed plate from the plate work position, re-orientating the processed plate to its inverted orientation with its lid on, and transferring the processed plate to a plate store.

37. A method according to aspect 34 substantially as herein described in relation to the accompanying Figures.

38. A plate that has been inoculated and streaked by an apparatus according to any one of aspects 1 to 18.

39. A plate that has been inoculated and streaked by an apparatus according to any one of aspects 25 to 35

40. A plate that has been inoculated and streaked by a method according to any one of aspects 19 to 24.

41. A plate that has been inoculated and streaked by a method according to aspect 36 or aspect 37.

In conclusion, it must be appreciated that there may be other variations and modifications to the configurations described herein which are also within the scope of the present invention.

We claim:

1. An apparatus for automatically inoculating and streaking a medium in a plate, the streaking using a streaking applicator having a line of resiliently and flexibly supported spaced apart contact surfaces, the apparatus including:

(a) an inoculating and streaking station including:
a predetermined plate work position having a notional action line fixed in two dimensions (x, y); and
a rotatable platform;

(b) a sensor mounted relative to the notional action line and arranged to locate, prior to inoculation and within a sensing region of the notional action line, the surface of the medium in a plate positioned in the plate work position to thereby determine a surface positional reference in a third dimension (z) indicative of the height of the surface of the medium in that plate and to determine, prior to inoculation, an action line in three dimension (x, y, z) across the surface of the medium in the plate;

(c) a pipette robot system configured to move in two dimensions along the notional action line and in a third dimension to dispense inoculum, from a desired height relative to the action line, along the action line of the plate located in the plate work position; and (d) a streaking robot system configured to move the streaking applicator such that its line of spaced apart contact surfaces contacts at least the inoculum dispensed along the action line of the plate located in the plate work position, prior to rotation of the plate by the rotatable platform.

2. An apparatus according to claim 1, wherein the platform is movable into and out of the plate work position from a plate loading position, such that a plate supported by the platform becomes positioned in the plate work position operatively adjacent the sensor.

3. An apparatus according to claim 2, wherein the platform provides a datum level.

4. An apparatus according to claim 1, wherein the platform includes plate clamps for constant positioning the plate upon the platform.

5. An apparatus according to claim 1, wherein the rotatable platform includes a home flag which allows for the return of a rotated plate to a starting position.

6. An apparatus according to claim 1, wherein the plate work position is provided by the physical location in the apparatus of the sensor, the sensor being rigidly mounted to a main frame.

7. An apparatus according to claim 1, wherein the sensor is an ultrasonic sensing device having an ultrasonic beam focusing element to provide a focused beam on the surface of the medium of the plate in the predetermined plate work position.

8. An apparatus according to claim 7, wherein the beam is focused within a usable area that is central to the action line in its predetermined (x, y) position.

9. An apparatus according to claim 7, wherein the platform is movable into and out of the plate work position from a plate loading position, such that the plate supported in the platform becomes positioned in the plate work position operatively adjacent the sensor, wherein the platform provides a datum level, and wherein the sensor senses the surface and measures the distance to the surface, then referencing the measured distance to the datum level to determine a surface positional reference relative to the datum level in one dimension (z) for the surface, and uses the surface positional reference and the two fixed dimensions of the notional action line to determine the notional action line in three dimensions (x, y, z).

10. An apparatus according to claim 1, wherein the pipette robot system includes a disposable tip releasably secured to a pipette body.

11. An apparatus according to claim 1, wherein the platform is movable into and out of the plate work position from a plate loading position, such that the plate supported in the platform becomes positioned in the plate work position operatively adjacent the sensor, wherein the platform provides a datum level, and wherein the pipette robot system is programmable for various inoculum volumes, and includes a positional height (z direction) referencing system relative to the locating datum surface of the platform.

12. An apparatus according to claim 1, wherein the streaking robot system includes an applicator handling head suitable to obtain and hold a streaking applicator, and then transfer that applicator to the plate work position adjacent a positioned plate.

13. An apparatus according to claim 12, wherein the applicator handling head is able to move the applicator in the z direction to locate the line of contact surfaces of the applicator along the notional action line on the surface of the medium in a positioned plate.

14. An apparatus according to claim 12, wherein the application handling head of the streaking robot system includes an openable clamp that is able to grasp a mounting portion of a streaking applicator.

15. An apparatus according to claim 14, wherein the openable clamp of the streaking robot system includes a release catch which is able to interact with a fixed eject pin located near an applicator disposal chute, such that engagement of the pin with the latch causes the clamping member to release the applicator and allow it to fall into the applicator disposal chute.

16. An apparatus for automatically inoculating and streaking a medium in a plate, the streaking using a streaking applicator having a line of resiliently and flexibly supported spaced apart contact surfaces, the apparatus including:

(a) an inoculating and streaking station including:
a predetermined plate work position having a notional action line fixed in two dimensions (x, y); and
a rotatable platform;

(b) a sensor mounted relative to the notional action line and arranged to locate, prior to inoculation and within a sensing region of the notional action line, the surface of the medium in a plate positioned in the plate work position to thereby determine a surface positional reference in a third dimension (z) indicative of the height of the surface of the medium in that plate and to determine, prior to inoculation, an action line in three dimension (x, y, z) across the surface of the medium in the plate;

(c) a pipette robot system configured to move in two dimensions along the notional action line and in a third dimension to dispense inoculum, from a desired height relative to the action line, along the action line of the plate located in the plate work position; and (d) a streaking robot system configured to move the streaking applicator such that its line of spaced apart contact surfaces contacts at least the inoculum dispensed along the action line of the plate located in the plate work position, prior to rotation of the plate by the rotatable platform; and (e) an alarm configured to be activated if the surface positional reference (z) is determined to be above an upper detection limit or below a lower detection limit.

* * * * *